(12) United States Patent
Klatzmann et al.

(10) Patent No.: US 9,801,927 B2
(45) Date of Patent: Oct. 31, 2017

(54) PHARMACEUTICAL COMPOSITIONS COMPRISING A POLYPEPTIDE COMPRISING AT LEAST ONE CXXC MOTIF AND HETEROLOGOUS ANTIGENS AND USES THEREOF

(75) Inventors: David Klatzmann, Paris (FR); Eliane Piaggio, Paris (FR); Hugo Daniel Luján, Córdoba (AR)

(73) Assignees: CENTRE NATIONAL DE LA RECHERCHE SCIENTIFIQUE-CNRS, Paris (FR); UNIVERSITE PIERRE ET MARIE CURIE (PARIS 6), Paris (FR); ASSITANCE PUBLIQUE HOPITAUX DE PARIS, Paris (FR); CONSEJO NACIONAL DE INVESTIGACIONES CIENTIFICAS Y TECNICAS (CONICET), Buenos Aires (AR); UNIVERSIDAD CATOLICA DE CORCOBA (UCC), Cordoba (AR)

( * ) Notice: Subject to any disclaimer, the term of this patent is extended or adjusted under 35 U.S.C. 154(b) by 74 days.

(21) Appl. No.: 13/636,482

(22) PCT Filed: Mar. 29, 2011

(86) PCT No.: PCT/EP2011/054866
§ 371 (c)(1),
(2), (4) Date: Dec. 21, 2012

(87) PCT Pub. No.: WO2011/120994
PCT Pub. Date: Oct. 6, 2011

(65) Prior Publication Data
US 2013/0095133 A1 Apr. 18, 2013

(30) Foreign Application Priority Data
Mar. 29, 2010 (EP) .................................... 10305317

(51) Int. Cl.
| | | |
|---|---|---|
| *A61K 39/395* | (2006.01) | |
| *A61K 39/00* | (2006.01) | |
| *A61K 39/145* | (2006.01) | |
| *A61K 39/385* | (2006.01) | |
| *C07K 14/44* | (2006.01) | |
| *C12N 7/00* | (2006.01) | |
| *A61K 39/12* | (2006.01) | |
| *B82Y 5/00* | (2011.01) | |

(52) U.S. Cl.
CPC .............. *A61K 39/00* (2013.01); *A61K 39/12* (2013.01); *A61K 39/145* (2013.01); *A61K 39/385* (2013.01); *C07K 14/44* (2013.01); *C12N 7/00* (2013.01); *A61K 2039/5258* (2013.01); *A61K 2039/542* (2013.01); *A61K 2039/6031* (2013.01); *B82Y 5/00* (2013.01); *C07K 2319/00* (2013.01); *C12N 2740/13023* (2013.01); *C12N 2760/16123* (2013.01); *C12N 2760/16134* (2013.01); *C12N 2810/6072* (2013.01); *Y10S 977/773* (2013.01)

(58) Field of Classification Search
None
See application file for complete search history.

(56) References Cited

U.S. PATENT DOCUMENTS 6,187,310 B1 * 2/2001 Mann et al. ............... 424/185.1

FOREIGN PATENT DOCUMENTS

| EP | 2199301 | | 6/2010 | |
|---|---|---|---|---|
| WO | WO 00/55326 | * | 9/2000 | ............. C12N 15/31 |
| WO | 02/34893 | | 5/2002 | |
| WO | WO 2004/009116 A2 | | 1/2004 | |
| WO | WO 2006/026746 A2 | | 3/2006 | |
| WO | 2006/059141 | | 6/2006 | |
| WO | WO 2007/122388 A2 | | 11/2007 | |
| WO | 2008/094197 | | 8/2008 | |

OTHER PUBLICATIONS

Stagers et al.: (International Journal of Parasitology, Pergamon Press, GB, vol. 27, No. 8, Aug. 1, 1997.).*
Davids et al. (PloS ONE, issue 1, e44, Dec. 2006).*
Carranza et al., "New insights regarding the biology of Giardia lamblia," Microbes and Infection, 12(1):71-80 (2010) XP026824317.
International Preliminary Report on Patentability in PCT/EP2011/054866 dated Jul. 2, 2012.
International Search Report and Written Opinion in PCT/EP2011/054866 dated May 16, 2011.
Jespersgaard et al., "Protective immunity against *Streptococcus mutans* infection in mice after intranasal immunization with the glucan-binding region of *S. mutans* glucosyltransferase," Infection and Immunity, 67(12):6543-6549 (1999) XP007918477.
Marti et al., "Conformationally correct expression of membrane-anchored Toxoplasma gondii SAG1 in the primitive protozoan Giardia duodenalis," Infection and Immunity, 70(2):1014-1016 (2002) XP007913876.
Stager et al., "Systemic and local antibody response in mice induced by a recombinant peptide fragment from Giardia lamblia variant surface protein (VSP) H7 produced by a *Salmonella typhimurium* vaccine strain," Int. J. Parasitology, 27(8):965-971 (1997) XP002423505.

(Continued)

*Primary Examiner* — Ja'na Hines
*Assistant Examiner* — Khatol Shahnan Shah
(74) *Attorney, Agent, or Firm* — RatnerPrestia

(57) ABSTRACT

The invention relates to pharmaceutical compositions using a polypeptide comprising at least one CXXC motif, such as *Giardia* parasite's variable surface proteins (VSP) or a fragment thereof to raise by oral or mucosal vaccination an immune response against a heterologous selected antigen, such as tumor antigen, microbial antigen or other antigen.

11 Claims, 5 Drawing Sheets

(56) References Cited

OTHER PUBLICATIONS

Figure 2:
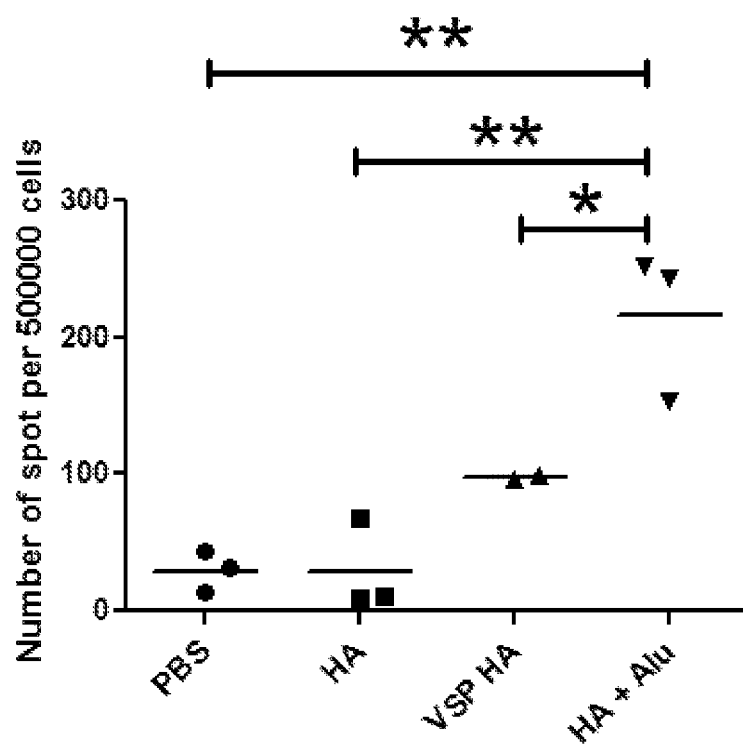

Szecsi et al., "Induction of neutralizing antibodies by virus-like particles harbouring surface proteins from highly pathogenic H5N1 and H7N1 influenza viruses," Virol. J., 3(1):70 (2006) XP021019376.

Adam et al., "The *Giardia lamblia* vsp gene repertoire: characteristics, genomic organization, and evolution," BMC Genomics Jul. 9, 2010, 11:424.

Franzén et al., "Draft Genome Sequencing of *Giardia intestinalis* Assemblage B Isolate GS: Is Human Giardiasis Caused by Two Different Species?," PLoS Pathogens, vol. 5, Issue 8, Aug. 2009.

Hlavsa et al., "Giardiasis Surveillance—United States, 1998-2002," MMWR Surveillance Summaries, Jan. 28, 2005, 54(SS01); 9-16.

Jerlström-Hultqvist et al., "Genome analysis and comparative genomics of a *Giardia intestinalis* assemblage E isolate," BMC Genomics Oct. 7, 2010, 11:543.

Kirberg et al., "Thymic Selection of CD8+ Single Positive Cells with a Class II Major Histocompatibility Complex-restricted Receptor," J. Exp. Med. Jul. 1, 1994, vol. 180, 25-34.

Lavelle et al., "Delivery systems and adjuvants for oral vaccines," Expert Opin. Drug Deliv. (2006), 3(6):747-762.

Morrison et al., "Genomic Minimalism in the Early Diverging Intestinal Parasite *Giardia lamblia*," Science Sep. 28, 2007, vol. 317, 1921-1926.

Nash, "Antigenic variation in *Giardia lamblia* and the host's immune response," Phil. Trans. R. Soc. Lond. B 1997, 352, 1369-1375.

Nash, "Surface antigenic variation in *Giardia lamblia*," Molecular Microbiology 2002, 45(3), 585-590.

Rivero et al., "Disruption of antigenic variation is crucial for effective parasite vaccine," Nature Medicine May 2010, vol. 16, No. 5, 551-557.

\* cited by examiner

Figure 1

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid

<400> SEQUENCE: 1

Cys Xaa Xaa Cys
1

<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Gly Gly Cys Tyr
1

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Cys Arg Gly Lys Ala
1               5
```

PHARMACEUTICAL COMPOSITIONS COMPRISING A POLYPEPTIDE COMPRISING AT LEAST ONE CXXC MOTIF AND HETEROLOGOUS ANTIGENS AND USES THEREOF

The present application is filed pursuant to 35 U.S.C. 371 as a U.S. National Phase application of International Patent Application No. PCT/EP2011/054866, which was filed Mar. 29, 2011, claiming the benefit of priority to European Patent Application No. 10305317.9, which was filed on Mar. 29, 2010. The entire text of the aforementioned applications is incorporated herein by reference in its entirety.

FIELD OF THE INVENTION

The present invention relates to pharmaceutical compositions, and methods of using thereof, to produce, modify or regulate an immune response in a subject.

The present invention relates, more particularly, to pharmaceutical compositions using a polypeptide comprising at least one CXXC motif, such as *Giardia* parasite's variable surface proteins (VSP) or a fragment thereof (e.g. the extracellular domain of a *Giardia* VSP or a fragment thereof) to raise by oral or mucosal vaccination an immune response against a heterologous selected antigen, such as tumor antigen, microbial antigen or other antigen.

BACKGROUND OF THE INVENTION

Various strategies have been proposed in the art to rise an immune response in a subject, such as direct administration of an antigen, ex vivo stimulation and expansion of immune cells (such as T lymphocytes or dendritic cells, for instance), injection of genetically- or chemically-modified cancer cells, administration of inactivated viruses and gene therapy using nucleic acids encoding particular antigens or cytokines.

While these various approaches allow the generation of an immune response against certain types of antigens or pathogenic agents, there is still a need for better methods of eliciting, regulating or stimulating an immune response. In particular, there is a need for simple methods of generating efficient immune responses, such as efficient cellular and/or humoral immune responses, against a variety of antigens, such as tumor antigens, viral antigens or other antigens from pathogenic agents, most particularly, by oral administration.

Indeed, most commercial vaccines available today are delivered by injection, with problems of safety, patient acceptability and morbidity and which makes mass immunization more costly and less safe, particularly in resource-poor developing countries. Therefore, oral delivery offers a number of significant advantages over other routes of administration and notably compared with parenteral vaccines (simple administration and improved safety). In addition, unlike systemic immunisation, oral delivery can induce mucosal immune responses.

Thus, orally delivered vaccines are processed and presented by the digestive tract's immune system, often referred to as the gut-associated lymphoid tissue (GALT). The GALT is a complex system consisting of inductive sites (where antigens are encountered and responses are initiated) and effector sites (where local immune responses occur) linked by a homing system, whereby cells activated by antigen in the GALT migrate to the circulation and, subsequently, to the mucosa (Lavelle et al.; 2006). As a result, oral vaccination can induce immune responses locally in the gut and at distant mucosal sites, as well as systemic humoral and cellular immune responses. Oral vaccination typically generates a large amount of secretory IgA (sIgA), which plays a major role in mucosal defense.

Yet, even if the oral route of vaccine delivery represents the ideal means of delivering prophylactic and therapeutic vaccines, offering significant advantages over systemic delivery, the oral route is also the most difficult because of the numerous barriers posed by the gastrointestinal tract. To facilitate effective immunisation with peptide and protein vaccines, antigens must be protected, uptake enhanced and the innate immune response activated. Thus, numerous delivery systems and adjuvants have been evaluated for oral vaccine delivery, including live vectors, inert particles and bacterial toxins. However, developments in oral vaccines have been until now disappointing since no efficient oral immunisation has been obtained by using proteins or Virus-like Particles (VLP) alone.

Consequently, there is still a need for better methods of eliciting, regulating or stimulating an immune response, such as efficient cellular and/or humoral immune responses, against a variety of antigens, such as tumor antigens, viral antigens or other antigens from pathogenic agents by oral or mucosal administration.

SUMMARY OF THE INVENTION

The present invention now provides such a novel, alternative and improved method of causing, regulating or stimulating an immune response in a subject by oral or mucosal administration.

The present invention is based, more particularly, on a new concept of using a polypeptide comprising at least one CXXC motif, wherein C represents a cysteine residue and X any aminoacid residue, such as a *Giardia* parasite's variable surface protein (VSP) or a fragment thereof (e.g. the extracellular domain of a *Giardia* VSP or a fragment thereof) to raise by oral or mucosal administration an immune response against selected antigen, in particular a cellular and/or a humoral immune response, in order to treat or prevent disease caused by such selected antigen in a subject.

The present invention also discloses related pharmaceutical compositions comprising vector particles and/or fusion proteins, their preparation and uses, which allow the generation of improved immune responses against antigens by oral or mucosal administration.

In a first aspect, the present invention thus relates to a pharmaceutical composition comprising at least:
  a polypeptide comprising at least one CXXC (SEQ ID NO.: 1) motif, wherein C represents a cysteine residue and X any aminoacid residue, and
  a heterologous antigen.

In a second aspect, the present invention relates to a fusion protein comprising a polypeptide comprising at least one CXXC (SEQ ID NO.: 1) motif as defined above and retaining the ability to attach to epithelial cells of the gut and a heterologous antigen.

In a third aspect, the present invention relates to a polypeptide comprising at least one CXXC (SEQ ID NO.: 1) motif as defined above and retaining the ability to attach to epithelial cells of the gut bound to a vector particle.

In a fourth aspect, the present invention relates to a pharmaceutical composition for use in the treatment or prevention of a disease, a disorder or physiologic conditions in a subject.

In fifth aspect, the present invention relates to the use of a polypeptide comprising at least one CXXC (SEQ ID NO.:

1) motif as defined above such as a Giardia VSP or a fragment thereof as a carrier for a heterologous antigen for presentation and vaccination, particularly oral or mucosal vaccination.

DETAILED DESCRIPTION OF THE INVENTION

The inventors demonstrate for the first time that a protein or a polypeptide comprising at least one CXXC (SEQ ID NO.: 1) motif, wherein C represents a cysteine residue and X any aminoacid residue, such as *Giardia* variable surface proteins (VSP) (e.g. the extracellular domain of a *Giardia* VSP or a fragment thereof) could be used by the oral route as carrier of candidate vaccinal antigen or to induce protective immunity. Moreover, the inventors demonstrate that such polypeptides such as extracellular domain of VSPs, which are resistant to proteases, different pHs, and able to attach to epithelial cells of the gut, are useful to form Virus-Like Particles (VLPs) suitable to be administered orally.

Definitions

Throughout the specification, several terms are employed and are defined in the following paragraphs.

As used herein, the term "immunogenic" designates a product, composition or method that elicits, causes, stimulates or regulates an immune response or reaction. The immunogenic composition is thus any composition that modifies the activity of an immune system in a subject or in vitro. This includes protective immune responses, cellular immune responses, antibody responses, neutralizing immune responses, modification in antibody levels, modification in immune cell levels, etc.

As used herein, the term "antigen" refers to a molecule capable of being specifically bound by an antibody or by a T cell receptor (TCR) if processed and presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant or require that the antigen is presented in accordance with the present invention. An antigen can have one or more epitopes or antigenic sites (B- and T-epitopes). The term "specifically bound," as used herein, is meant to indicate that the antigen will preferably react, typically in a highly selective manner, with its corresponding antibody or TCR and not with the multitude of other antibodies or TCRs which may be evoked by other antigens.

As used herein, the term "epitope" refers to continuous or discontinuous portions of a polypeptide or of a non-peptidic molecule having antigenic or immunogenic activity in an animal, preferably a mammal, and most preferably in a human. An epitope is recognized by an antibody or a T cell through its T cell receptor in the context of an MHC molecule. An "immunogenic epitope" as used herein, is defined as a portion of a polypeptide or of a non-peptidic molecule that elicits an antibody response or induces a T-cell response in an animal, as determined by any method known in the art. The term "antigenic epitope" as used herein, is defined as a portion of a protein or of a non-peptidic molecule to which an antibody can immunospecifically bind its antigen as determined by any method well known in the art. Immunospecific binding excludes non-specific binding but does not necessarily exclude cross-reactivity with other antigens. Antigenic epitopes need not necessarily be immunogenic. Antigenic epitopes can also be T-cell epitopes, in which case they can be bound immunospecifically by a T-cell receptor within the context of an MHC molecule.

As used herein, the term "heterologous antigen" refers to an antigen that is heterologous with respect with the parasite *Giardia* (notably *Giardia lamblia*) or other microorganism as defined in the context of the present invention and therefore such heterologous antigen is not derived from the parasite *Giardia* or said other microorganisms. Within the context of the present invention, the term "heterologous antigen" thus embraces a plant, an animal, a parasitic (e.g. other than one derived from *Giardia*), a bacterial, a viral, a tumor antigen, a self-antigen or a chemical molecule. However, it should be noted that said heterologous antigen may be derived from *Giardia* if the polypeptide of the invention is derived from another microorganism such as for instance *Tetrahymena, Paramecium, Entamoeba*.

As used herein, the terms "*Giardia*" or "*Giardia* parasite" refer to a genus of anaerobic flagellated protozoan parasites of the phylum Metamonada that colonise and reproduce in the small intestines of several vertebrates, causing giardiasis. World-wide, giardiasis is common among people with poor faecal-oral hygiene, and major modes of transmission include contaminated water supplies or sexual activity. Flagellated *Giardia* trophozoites attach to epithelial cells of the small intestine (i.e. the surface of the intestinal mucosa), where they can cause disease without triggering a pronounced inflammatory response (Rivero et al., 2010). There are no known virulence factors or toxins, and variable expression of surface proteins allow evasion of host immune responses and adaptation to different host environments (Rivero et al. 2010). Their life cycle alternates between an actively swimming trophozoite and an infective, resistant cyst. The *Giardia* parasite infects humans, but is also one of the most common parasites infecting cats, dogs and birds. Mammalian hosts also include cows, beavers, deer, and sheep. Thus, the term "*Giardia*" encompasses different species, including *Giardia lamblia* and *Giardia muris*.

As used herein, the term "*Giardia lamblia*" (also called *Giardia intestinalis* or *Giardia duodenalis*) refers to one of the most common intestinal parasites of humans. *Giardia lamblia* is the most prevalent parasitic protist in the United States, where its incidence may be as high as 0.7% (Hlaysa et al. 2005).

As used herein, the terms "variable surface protein" or "VSP" refer to a polypeptide that covers the entire surface of the *Giardia* parasite and are the major antigens recognized by the host immune system. VSPs are cysteine-rich proteins with frequent CXXC (SEQ ID NO.: 1) motifs (where X is any amino acid) that have several particular characteristics, including in some VSP the presence of CXC motifs, a *Giardia*-specific Zinc-finger motif, and GGCY (SEQ ID NO.: 2) motifs (Nash, 2002; Adam et al, 2010). More precisely, VSP are type 1 integral membrane proteins that vary in size from 20 to 200 kDa; possess a variable amino-terminal cysteine-rich region (extracellular domain that represents the host/parasite interface and confers to the protein resistance to proteolytic digestion and low pH), and a conserved carboxy-terminal region that includes a hydrophobic transmembrane region and a short cytosolic tail comprising only 5 amino acids (CRGKA (SEQ ID NO.: 3)), which are not "seen" by the immune system. Only one VSP is expressed at any given time on the surface of each parasite as described in Nash (1997). Within the context of the present invention, it is intended that the term "variable surface protein" includes any variable surface protein of the complete repertoire of *Giardia* VSPs, notably *Giardia lamblia*. Actually, *Giardia* parasites encodes a repertoire of about 200 genes encoding VSPs as described in Morrison et al. (2007) and Adam et al. (2010) for the assemblage A, and two reports of Svard's group describing the VSP repertoire of isolates derived from assemblages B and E (Jerlström-Hultqvist et al. (2010) and Franzen et al. (2009). The extracellular domain of VSP allows the parasite to survive the hostile environment of the upper small intestine. VSPs are very resistant to variable pHs (reactivity to a conformational epitope by a monoclonal antibody (mAb) directed to a particular VSP remain unaltered between pH 2 and 12), and digestion by trypsin and several other proteases. In addition, VSP remain attached to the enteric mucosa after the trophozoites have attached to it (Rivero et al., 2010).

It must be further noted that polypeptide comprising at least one CXXC (SEQ ID NO.: 1) motif, wherein C represents a cysteine residue and X any aminoacid residue, such as *Giardia* VSPs or VSP-like proteins of other microorganisms may also be generated in vitro by genetic manipulation and produced in heterologous systems. Therefore, chemically- or cell-produced polypeptides, including those with amino acid variations not found in the wild type parasites (for instance variants of *Giardia* VSP) are encompassed. VSP may thus be prepared by any well-known procedure in the art, such as solid phase synthesis, liquid phase synthesis or genetic engineering.

The VSP of the invention may optionally comprise chemical modifications. Chemical modifications aimed at obtaining proteins with increased protection of the proteins against enzymatic degradation in vivo, and/or increased capacity to cross membrane barriers, thus increasing its half-life and maintaining or improving its biological activity. Any chemical modification known in the art can be employed according to the present invention. Such chemical modifications include but are not limited to:

- modifications to the N-terminal and/or C-terminal ends of the proteins such as e.g. N-terminal acylation (preferably acetylation) or desamination, or modification of the C-terminal carboxyl group into an amide or an alcohol group;
- modifications at the amide bond between two amino acids: acylation (preferably acetylation) or alkylation (preferably methylation) at the nitrogen atom or the alpha carbon of the amide bond linking two amino acids;
- modifications at the alpha carbon of the amide bond linking two amino acids such as e.g. acylation (preferably acetylation) or alkylation (preferably methylation) at the alpha carbon of the amide bond linking two amino acids.
- chirality changes such as e.g. replacement of one or more naturally occurring amino acids (L enantiomer) with the corresponding D-enantiomers;
- retro-inversions in which one or more naturally-occurring amino acids (L-enantiomer) are replaced with the corresponding D-enantiomers, together with an inversion of the amino acid chain (from the C-terminal end to the N-terminal end); and/or
- azapeptides wherein one or more alpha carbons are replaced with nitrogen atoms.

The term "protein" or its interchangeably used term "polypeptide" as used herein refer to a molecule composed of monomers (amino acids) linearly linked by amide bonds (also known as peptide bonds). Post-translational modifications of the polypeptide, for example, glycosylations, acetylations, phosphorylations, and the like are also encompassed. The terms "protein" or "polypeptide" also includes variants which should encompass any polypeptide comprising, or alternatively or preferably consisting of, any natural or genetically engineered polypeptide having more than 70%, preferably more than 80%, even more preferably more than 90%, again more preferably more than 95%, and most preferably more than 97% amino acid sequence identity with the sequence of the polypeptide. Preferred methods of generating a variant of a polypeptide is by genetic engineering, preferably by insertion, substitution, deletion or a combination thereof. When the term "variant of a protein" applies, in accordance with the present invention, to the antigen, such variant should be capable of inducing the production of antibody, or stimulation of T cell, in vivo. When the term "variant of a protein" applies, in accordance with the present invention, to the *Giardia* VSP or VSP-like protein of other microorganisms, such variant should be capable of retaining the ability to attach to cells, particularly mucosal cells, more particularly epithelial cells of the gut and eventually inducing an immune response per se.

As used herein, when the term "a fragment of a protein" applies, in accordance with the present invention, to the VSP, or its interchangeably used term "a fragment of a polypeptide" such fragment should encompass any polypeptide comprising, or alternatively or preferably consisting of, at least 5, 6, 7, 8, 9, 10, 11, 12, 12, 13, 14, 15, 16, 17, 18, 19, 20, 25, 30, 40, 50, 100, 150, 200, 300, 400, 500 contiguous or discontinuous amino acids of the protein, polypeptide or antigen, as defined herein, as well as any polypeptide having more than 65%, preferably more than 80%, more preferably more than 90% and even more preferably more than 95% amino acid sequence identity thereto. When the term "fragment of a protein" applies, in accordance with the present invention, to the antigen, such fragment should be capable of inducing the production of antibody, or stimulation of T cell, in vivo. Thus, a fragment of a protein should comprise at least one immunogenic epitope. When the term "fragment of a protein" applies, in accordance with the present invention, to the *Giardia* VSP or VSP-like protein of other microorganisms, such fragment should be capable of retaining the ability to attach to cells, particularly mucosal cells, more particularly epithelial cells of the gut and eventually inducing an immune response per se.

As used herein, the term "bound" refers to binding that may be covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds, carbon-phosphorus bonds, and the like. The term also includes the enclosement, or partial enclosement, of a substance (e.g. the heterologous antigen). The term "bound" is broader than and includes terms such as "coupled", "fused", "enclosed", "packaged", "pseudotyped", "expressed in a lipid bilayer" and "attached."

As used herein, the term "fusion" refers to the combination of amino acid sequences of different origin in one polypeptide chain by in-frame combination of their coding nucleotide sequences. It must be noted that more than one nucleotide sequence may encode one given amino acid sequence due to the degeneracy of the genetic code. The term "fusion" explicitly encompasses internal fusions, (i.e.

insertion of sequences of different origin within a polypeptide chain, in addition to fusion to one of its termini).

As used herein, the term "conjugate" refers to the product of conjugation between (a) an *Giardia* VSP or a fragment thereof, and (b) an organic molecule (e.g. an heterologous antigen which consists of a non-protein antigen), wherein the elements (a) and (b) are bound to each other. Such elements (a) and (b) may be bound for instance by a linker.

The term "linking sequence" or its interchangeably used term "linker" as used herein, refer to a molecular entity that covalently links protein or non-protein antigens such as a nicotine molecule to a polypeptide as well as a vector particle to a polypeptide. The linker may for instance comprise a thiol group, an alkyl group, a glycol group or a peptide group. Linkers include cross-linking molecules and some examples are listed in the in the international patent application published under no WO 2004/009116, which is incorporated therein by reference.

As used herein, "vector particle" denotes any particle liable to display a *Giardia* VSP or a fragment thereof and/or the heterologous antigen at its surface. Within the context of the present invention, it is intended that the term "vector particle" includes viral vector particle, virus-like particle (VLP) and nanoparticles.

The term "viral vector particle" as used herein refers to the morphological form of a virus. In some virus types it comprises a genome surrounded by a protein capsid; others have additional structures (e.g., envelopes, tails, etc.).

The term "Virus-Like Particle" (VLP), as used herein, refers to a structure resembling a virus particle. A virus-like particle in accordance with the invention is non-replicative since it lacks all or part of the viral genome, typically and preferably lacking all or part of the replicative and infectious components of the viral genome. The term "non-replicative", as used herein, refers to being incapable of replicating the genome comprised or not in the VLP.

Pharmaceuticals Compositions of the Invention

In a first aspect, the present invention relates to a pharmaceutical composition, preferably immunogenic, comprising at least:
 a polypeptide comprising at least one CXXC (SEQ ID NO.: 1) motif, wherein C represents a cysteine residue and X any aminoacid residue, and
 a heterologous antigen.

When a pharmaceutical composition of the invention is administered to an individual, it may be in a form which contains salts, buffers, adjuvants, carriers or other substances which are desirable for improving the efficacy of the composition. Examples of pharmaceutically materials suitable for use in preparation of pharmaceutical compositions are provided in numerous sources including REMINGTON'S PHARMACEUTICAL SCIENCES (Osol, A, ed., Mack Publishing Co., (1990)). "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Furthermore, the pharmaceutical compositions may comprise additional adjuvants or immunogenic or biologically active agents. However, in one preferred embodiment, the pharmaceutical compositions are devoid of adjuvant, since an advantageous feature of the invention is the high immunogenicity of the composition, even in the absence of adjuvants. The absence of an adjuvant, furthermore, minimizes the occurrence of unwanted inflammatory T-cell responses representing a safety concern in the vaccination.

The pharmaceutical compositions of the invention are preferably formulated for an oral or a mucosal administration. The doses used for the oral or a mucosal administration can be adapted as a function of various parameters, and in particular as a function of the mode of the relevant pathology, or alternatively of the desired duration of treatment.

The pharmaceutical composition may be administered to any suitable mucosa, and the administration includes oral (via the mucosa of the digestive system), nasal, vaginal, sublingual, ocular, rectal, urinal, intramammal, pulmonal, otolar (i.e. via the ear) and buccal administration, preferably buccal or sublingual administration (oromucosal administration).

Upon formulation, pharmaceutical compositions will be administered in a manner compatible with the dosage formulation and in such amount as is therapeutically effective. The formulations are easily administered in a variety of dosage forms, such as the type of, e.g. tablets or other solids for oral or a mucosal administration; time release capsules; and any other form currently used. Accordingly, the pharmaceutical composition may be in the form of a spray, an aerosol, a mixture, a suspension, a dispersion, an emulsion, a gel, a paste, a syrup, a cream, an ointment, implants (ear, eye, skin, nose, rectal, and vaginal), intramammary preparations, vagitories, suppositories, or uteritories). In certain embodiments, the use of liposomes is contemplated. The formation and use of liposomes are known to those of skill in the art.

As previously mentioned, in a preferred embodiment, the pharmaceutical composition is suitable for oral administration.

More particularly, the pharmaceutical composition is formulated so that the heterologous antigen and the polypeptide are resistant to enzymatic and chemical degradation of the upper gastrointestinal tract, when necessary. Moreover, it should be noted that the polypeptide should be able to attach to cells, more particularly epithelial cells of the gut. Thus, in one embodiment, the polypeptide is able to attach to epithelial cells of the gut and the composition is formulated so that the heterologous antigen and the polypeptide are resistant to enzymatic and chemical degradation of the upper gastrointestinal tract, when necessary.

In one embodiment, the polypeptide consists of a polypeptide comprising at least two CXXC (SEQ ID NO.: 1) motifs separated by at least 2 amino acids.

Accordingly, the two CXXC (SEQ ID NO.: 1) motifs are separated by an amino sequence comprising from 3 to 20 amino acids, preferably from 5 to 8 amino acids.

It should be noted that the amino acids separating the at least two CXXC (SEQ ID NO.: 1) motifs may be any amino acid residue.

In another one embodiment, the polypeptide comprises from 1 to 10 CXXC (SEQ ID NO.: 1) motifs, from 1 to 20 CXXC (SEQ ID NO.: 1) motifs, from 1 to 30 CXXC (SEQ ID NO.: 1) motifs, from 1 to 40 CXXC (SEQ ID NO.: 1) motifs, from 1 to 50 CXXC (SEQ ID NO.: 1) motifs, from 1 to 60 CXXC (SEQ ID NO.: 1) motifs, from 1 to 70 CXXC (SEQ ID NO.: 1) motifs, from 1 to 80 CXXC (SEQ ID NO.: 1) motifs, from 1 to 90 CXXC (SEQ ID NO.: 1) motifs or from 1 to 100 CXXC (SEQ ID NO.: 1) motifs.

Thus, the polypeptide may for instance comprise 1, 2, 3, 4, 5, 6, 7, 8, 9, 10, 11, 12, 13, 14, 15, 20, 25, 30, 35, 40, 45, 50, 55, 60, 65 or 70 CXXC (SEQ ID NO.: 1) motifs.

In one particular embodiment, the polypeptide as defined above is a variable surface protein (VSP), a VSP-like protein of a microorganism or a fragment thereof.

Accordingly, the microorganism is preferably selected in the group consisting of *Giardia, Tetrahymena, Paramecium* and *Entamoeba* species.

In one preferred embodiment, the polypeptide is the extracellular domain of a *Giardia* VSP or a fragment thereof (since said extracellular domain is the amino-terminal cysteine rich region comprising multiple CXXC (SEQ ID NO.: 1) motifs of the *Giardia* VSP protein).

Indeed, the extracellular domain of a *Giardia* VSP is the domain resistant to the pH, temperature and proteolytic digestion.

Accordingly, in another preferred embodiment, the polypeptide according to the invention comprises only the extracellular domain of a *Giardia* VSP or a fragment thereof. The transmembrane region and the cytoplasmic tail of a *Giardia* VSP are thus eliminated.

It should be noted that the peptide signal may also be removed.

Variable Surface Protein (VSP)

Accordingly, the variable surface protein (VSP) or a fragment thereof may be chosen among the complete repertoire of VSPs, which are encoded at the DNA level in the genome of the parasite. This repertoire is composed of about 200 homologous VSP-encoding genes (vsps), which varies in different *Giardia* isolates. It should be further noted that variants of VSP may be also used in the composition according to the invention.

As above-mentioned, the *Giardia* VSPs and more particularly the extracellular domain of the *Giardia* VSPs comprise multiple CXXC (SEQ ID NO.: 1) motifs, preferably multiple CXXC (SEQ ID NO.: 1) motifs separated by several amino acids, from 3 to 20 amino acids and more particularly from 5 to 8 amino acids, (as observed by multiple sequence alignments).

In a particular embodiment, the *Giardia* parasite is *Giardia lamblia*.

In a preferred embodiment, the *Giardia* VSP is selected from the group consisting of VSP9B10, VSP1267, VSPA6, VSPS1, VSPS2, VSPS3, VSPS4, VSPS5, VSPS6, VSPS7, VSPS8, VSPAS1, VSPAS2, VSPAS3, VSPAS4, VSPAS5, VSPAS6, VSPAS7, VSPAS8, VSPAS9, VSPAS10, VSPAS11, VSPAS12 and VSPH7 of *Giardia lamblia*.

VSP-Like Domain

Accordingly, the VSP-like domain or a fragment thereof may be chosen among polypeptides derived from microorganisms other that *Giardia* sharing sequence homology and biochemical properties with *Giardia* and notably polypeptides containing multiple CXXC (SEQ ID NO.: 1) motifs, preferably multiple CXXC (SEQ ID NO.: 1) motifs separated by 5 to 8 amino acids. Indeed, alignment of the extracellular domain of VSP1267 sequence (query) with other VSP-like molecules sequences (results from domain architecture after BLASTP removing *Giardia* from the analysis) has led to observe the presence of multiple CXXC (SEQ ID NO.: 1) motif, notably separated by 5 to 8 amino acids, in proteins belonging to *Paramecium, Tetrahymena* and *Entamoeba* species. Thus, representative fragments of primary sequences of surface kinases of *Entamoeba* sp., and surface proteins of *Paramecium*. sp. and *Tetrahymena* sp. predict a conserved domain containing CXXC (SEQ ID NO.: 1) motifs in a VSP-like architecture (compared with *Giardia* VSP 1267, 9B10, and H7 as responsible for resistance to pH, temperature and proteolytic digestion.

In one embodiment, the *Tetrahymena* microorganism is *Tetrahymena thermophile*.

In another embodiment, the *Entamoeba* microorganism is *Entamoeba histolytica*.

In another embodiment, the *Paramecium* microorganism is *Paramecium tetraurelia*.

Heterologous Antigen

The heterologous antigen may consist of one naturally-occurring antigen, or a portion thereof, wherein the portion of the naturally-occurring antigen comprises or alternatively consists of at least one immunogenic epitope. Naturally-occurring antigen refers to an antigen which exists in nature, preferably exists in an organism, such as a plant, an animal, a parasite, a bacteria or a virus.

In preferred embodiments, the heterologous antigen is therefore selected from the group consisting of a plant, an animal, a parasitic, a bacterial, a viral, a self, a tumor antigen or a chemical molecule.

Thus, in one preferred embodiment of the present invention, the heterologous antigen is a non-self (or foreign) protein antigen, a fragment or a variant thereof.

Exemplary non-self protein antigens that are contemplated include a bacterial protein antigen, a viral protein antigen, a parasitic protein antigen, a tumor protein antigen, a mycoplasma protein antigen and an allergen protein antigen.

It must be further noted that the heterologous antigen may be constituted by the vector particle itself, when said particle (e.g. a Virus-Like Particle (VLP) as described below) is derived from a virus or comprises parts of a virus against which immunisation is sought. For instance, where the particle derives from a Human Immunodeficiency Virus (HIV), said particle may constitute the heterologous antigen.

In another preferred embodiment of the present invention, the heterologous antigen is a self protein antigen, a fragment or a variant thereof.

Indeed, diseases, particularly autoimmune diseases and chronic inflammatory diseases may be caused by the overproduction or malfunction of a self protein antigen.

Exemplary self protein antigens that are contemplated include cytokines, interleukins, hormones, growth factors, and receptors.

In still another preferred embodiment, the heterologous antigen is a non-protein antigen.

Exemplary non-protein antigens that are contemplated include a polysaccharide antigen, a lipid antigen, a nucleic acid antigen, a lipopolysaccharide antigen and a chemical molecule such as a drug.

Typical drugs, including both drugs of abuse and therapeutic drugs, alkaloids such as nicotine, steroids, toxins carbohydrates, aromatic compounds, including many pollutants, and other compounds against which an immune response can be raised.

Exemplary heterologous antigens (protein or non protein antigens) include, but are not limited, to those described in the international patent application N° WO 2006/02674.

In one embodiment, the polypeptide is bound to the heterologous antigen.

In another embodiment, the polypeptide is fused to the heterologous antigen.

In still another embodiment, the polypeptide is bound to a vector particle containing the heterologous antigen. Accordingly, the vector particle may be a viral particle, a Viral-Like Particle (VLP) or a nanoparticle.

In one particular embodiment, the vector particle is a VLP displaying at its surface the polypeptide of the invention.

In another particular embodiment, the heterologous antigen is contained inside or on the surface of the VLP.

Polypeptides According to the Invention Bound to the Heterologous Antigen.

Another aspect of the invention relates to the polypeptide comprising at least one CXXC (SEQ ID NO.: 1) motif according to the invention such as *Giardia* VSP or a fragment thereof bound to the heterologous antigen.

Polypeptides According to the Invention—Heterologous Antigen Fusion Proteins

When the heterologous antigen is a self or non-self protein antigen, the polypeptides according to the invention as defined above such as *Giardia* VSP or a fragment thereof may be fused with the heterologous antigen.

Therefore, one aspect of the invention relates thus to a fusion protein comprising a polypeptide comprising at least one CXXC (SEQ ID NO.: 1) motif, wherein C represents a cysteine residue and X any aminoacid residue, and retaining the ability to attach to epithelial cells of the gut, and a heterologous antigen.

In one embodiment, the polypeptide is a *Giardia* VSP or a fragment thereof.

In a particular embodiment, the polypeptide is the extracellular domain of a *Giardia* VSP or a fragment thereof.

The fusion proteins of the present invention may be prepared according to techniques known in the art (e.g. by use of recombinant nucleic acid technologies).

It must be noted that the present invention also relates to the polypeptides according to the invention such as the extracellular domain of *Giardia* VSPs or fragments thereof fused with heterologous protein antigens as defined above as well as to the nucleic acids which comprise sequences encoding them.

Polypeptides According to the Invention—Heterologous Antigen Conjugates

When the heterologous antigen is a non-protein antigen, the polypeptides according to the invention as defined above such as *Giardia* VSP or a fragment thereof may be covalently bound to the non-protein antigen by a linking sequence.

Therefore, another aspect of the invention relates thus to a conjugates comprising a polypeptide containing at least one CXXC (SEQ ID NO.: 1) motif, wherein C represents a cysteine residue and X any aminoacid residue, and retaining the ability to attach to epithelial cells of the gut, and a heterologous antigen.

In one embodiment, the polypeptide is a *Giardia* VSP or a fragment thereof.

In a particular embodiment, the polypeptide is the extracellular domain of a *Giardia* VSP or a fragment thereof.

The conjugates of the present invention may be prepared according to techniques known in the art (e.g. by technologies for coupling organic molecules to amino acids) and for example as described in the international patent application published under no WO 2004/009116, which is incorporated therein by reference.

It must be noted that the present invention also relates to the polypeptides according to the invention such as the extracellular domain of *Giardia* VSPs or fragments thereof conjugate to heterologous non-protein antigens as defined above.

Polypeptides According to the Invention Bound to a Vector Particle

In still another aspect, the polypeptides according to the invention as defined above such as *Giardia* VSP or a fragment thereof is bound to a vector particle.

In one embodiment, the polypeptide is a *Giardia* VSP or a fragment thereof.

In a particular embodiment, the polypeptide is the extracellular domain of a *Giardia* VSP or a fragment thereof.

In another embodiment, the heterologous antigen is bound to a vector particle.

In still another embodiment, the polypeptides according to the invention as defined above such as *Giardia* VSP or a fragment thereof and the heterologous antigen are both bound to the vector particle.

Accordingly, a fusion protein or a conjugate as described above may be bound to the vector particle.

Within the context of the present invention, the vector particle may be a viral vector particle, a Virus-Like Particle (VLP) or a nanoparticle.

In a particular embodiment, the vector particle is a virus-like particle (VLP).

Where Virus-Like Particles are being used, they may be prepared according to techniques known in the art and for example as described in the international patent application published under no WO 02/34893, which is incorporated therein by reference.

In a preferred embodiment, the VLP displays at its surface the polypeptide according to the invention such as a VSP of a *Giardia* parasite or a fragment thereof.

Thus, the polypeptide according to the invention such as a *Giardia* VSP or a fragment thereof may be exposed at the surface of the VLP. In this regard, the polypeptide according to the invention such as a *Giardia* VSP or a fragment thereof may be exposed through binding to various structures, such as to an envelope protein or a fragment thereof, a synthetic linker, or through chemical or enzymatic reaction, including antibody.

In one particular embodiment, the VLP comprises a modified envelope which may be a synthetic (chimeric) envelope comprising at least a portion of the trans-membrane domain of a retroviral envelope fused to the polypeptide according to the invention such as a *Giardia* VSP or a fragment thereof.

Accordingly, in a preferred embodiment, the VLP displays an envelope protein of a virus, such as an envelope protein from a vesicular stomatitis virus (VSV) or a fragment thereof (e.g. the transmembrane (TM) region of VSV G glycoprotein) fused with the polypeptide according to the invention such as a *Giardia* VSP or a fragment thereof exposed at the surface of the VLP, for instance by genetic or chemical fusion with the VSV envelope protein or a fragment thereof.

In another preferred embodiment, the VLP displays (i) an envelope protein of a virus, such as an envelope protein from a vesicular stomatitis virus (VSV) or a fragment thereof (e.g. the transmembrane (TM) region of VSV G glycoprotein) fused with the polypeptide according to the invention such as a *Giardia* VSP or a fragment thereof and (ii) the heterologous antigen.

In another particular embodiment, the synthetic envelope may be functionalised, thereby allowing the binding, to the synthetic envelope, through covalent or non-covalent interaction, of any selected molecule of interest. The functionalised envelope may comprise a linker wherein the linker allows (specific) binding of any selected molecule of interest. As an example, the envelope may comprise an avidine or biotine moiety, allowing specific binding thereto of a molecule. The bound molecule may be the polypeptide according to the invention such as a *Giardia* VSP or a fragment thereof as well as the heterologous antigen (i.e. non protein and protein antigen).

In one particular embodiment, the heterologous antigen is contained inside the VLP.

In a preferred embodiment, the Virus-Like Particle (VLP) comprises a retroviral or lentiviral Gag protein (such as the murine leukemia virus (MLV) or HIV Gag proteins, or fragments thereof), even more preferably a modified retroviral Gag protein. In a specific example, the Gag protein is a fusion protein comprising the heterologous antigen (i.e. influenza hemagglutinin (HA) or a fragment thereof (e.g. the SFE peptide consisting of peptide HA 111-119) leading to the fact that the heterologous antigen is contained inside the VLP.

Accordingly, the polypeptide according to the invention such as a *Giardia* VSP or a fragment thereof may form a protecting surface (as it occurs naturally in the parasite trophozoites) that allow for the correct delivery of the heterologous antigen into the mucosa (e.g. intestinal mucosa), without suffering degradation in the digestive track and at the same time the heterologous antigen may be adjuvanted by the VSP themselves, for the development of an appropriated protective immune response.

It must be noted that the present invention also relates to the Virus-Like Particle (VLP) described above according to the invention.

In another embodiment, the vector particle is a nanoparticle.

Within the context of the invention, the nanoparticles are of small size, small enough to be taken up by cells to allow the antigen to be presented on the cell surface. In preferred embodiments, the nanoparticles have a core with a mean diameter between 0.5 and 10 nm, more preferably between 1 and 2.5 nm.

The core of the nanoparticle may be a metallic core. Preferably, the metallic core comprises Au, Ag or Cu, for example an alloy selected from Au/Ag, Au/Cu, Au/Ag/Cu, Au/Pt, Au/Pd, Au/Ag/Cu/Pd, Au/Fe, Au/Cu, Au/Gd, Au/Fe/Cu, Au/Fe/Gd or Au/Fe/Cu/Gd.

Preferably, the nanoparticles of the invention are soluble in most organic solvents and especially water.

Where nanoparticles are being used, they may be prepared according to techniques known in the art and for example as described in the international patent application published under no WO 2007/122388, which is incorporated therein by reference.

In a preferred embodiment, the nanoparticle displays at its surface the polypeptide according to the invention such as a *Giardia* VSP or a fragment thereof.

In another preferred embodiment, the polypeptide according to the invention such as a *Giardia* VSP or a fragment thereof and the heterologous antigen are both bound to the surface of the nanoparticle.

Accordingly, a fusion protein or a conjugate as described above may be bound to the nanoparticle.

Therapeutic and Prophylactic Uses of the Pharmaceutical Compositions of the Invention In another aspect, the invention relates to a pharmaceutical composition of the invention for use in the treatment or the prevention of a disease, a disorder or physiologic conditions in a subject.

As used herein, the term "subject" denotes a mammal, such as a rodent, a feline, a canine, and a primate. Preferably a subject according to the invention is a human.

In the context of the invention, the term "treating" or "treatment", as used herein, means reversing, alleviating, inhibiting the progress of, or preventing the disorder or condition to which such term applies, or one or more symptoms of such disorder or condition.

Within the meaning of the invention, the term "preventing" or "prevention" with respect to an event is intended to mean the decrease of a risk of occurrence of said event.

Accordingly, a disease, a disorder or physiologic conditions considered in the invention may be selected in the group consisting of cancers, immunological diseases, autoimmune diseases, allograft rejections, viral diseases, such as influenza or AIDS, parasitic diseases such as malaria or trypanosome, bacterial infections, such as tuberculosis, allergies.

The invention also relates to a pharmaceutical composition of the invention for use as a vaccine.

The invention further relates to a pharmaceutical composition of the invention, polypeptide according to the invention such as a *Giardia* VSP or a fragment thereof bound to a heterologous antigen of the invention (including fusion proteins and conjugates), a polypeptide according to the invention such as a *Giardia* VSP or a fragment thereof bound to a vector particle of the invention for eliciting an immune response and/or enhancing an immune response.

The invention also relates to a method of treating or preventing a disease, a disorder or physiologic conditions in a subject, wherein said method comprises administering to said subject a therapeutically effective amount of the pharmaceutical composition of the invention.

In one preferred embodiment, the pharmaceutical composition is administrated by oral route.

In another embodiment, the pharmaceutical composition is administrated by mucosal route.

A "therapeutically effective amount" is intended for a minimal amount of active agent which is necessary to impart therapeutic benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder.

The invention also relates to a method of immunization of a subject, wherein said method comprises administering to said subject the pharmaceutical composition of the invention.

The invention further relates to the use of a polypeptide according to the invention such as a *Giardia* VSP or a fragment thereof as a carrier for a heterologous antigen presentation and vaccination, particularly oral or mucosal vaccination.

As previously mentioned, the polypeptide according to the invention such as a *Giardia* VSPs or fragments thereof favor a correct delivery of the heterologous antigen into the mucosa without suffering extensive degradation in the digestive track.

In an embodiment, the polypeptide is able to attach to epithelial cells of the gut and/or is resistant to enzymatic and/or chemical degradation of the upper gastrointestinal tract.

In one particular embodiment, the polypeptide is a variable surface protein (VSP), a VSP-like protein of a microorganism or a fragment thereof.

The invention will be further illustrated by the following figures and examples. However, these examples and figures should not be interpreted in any way as limiting the scope of the present invention.

FIGURES

Figure 1:
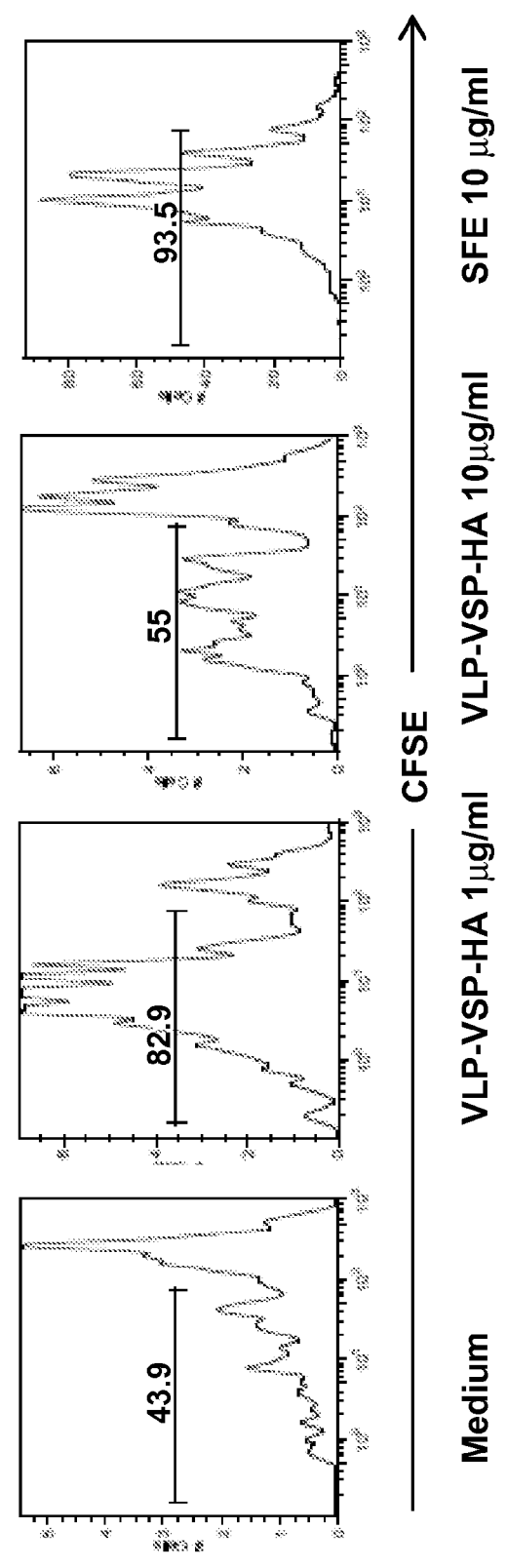

FIG. 1: CFSE labeled splenocytes from SFE-TCR mice ($10^6$/well) were cultured with CD11c purified DCs (5T:1DC ratio) for 72 h in medium alone, VLP-VSP-HA or recombinant SFE peptide (positive control) at the indicated concentrations. Histograms show T cell proliferation by CFSE dilution of SFE-specific T cells (gated using an anti-CD4+ antibody and the 6.5 anti-clonotypic antibody that specifically recognizes the transgenic T cells). Numbers indicate the percentage of divided cells.

FIG. 2: ELISPOT Assay (Oral immunization with HA-VSP fusion protein). HA-specific IFN-γ production was determined by a standard ELISPOT assay (Mabtech, Sophia Antipolis, France). Splenocytes (5×105 cells/well) were stimulated overnight at 37° C. in 5% CO2 with 1 µg/mL of HA protein. PBS or concanavalin A (5 µL/mL; ConA; Sigma-Aldrich) were used as negative and positive controls, respectively. After revelation, spots were counted using the AID ELISPOT reader (ELR03, AID AutoimmunDiagnostika, Strassberg, Germany) and unspecific spots detected in the negative controls were substracted. Symbols represent individual mice and horizontal lines represent the geometric mean of each group. *p<0.05, **p<0.01.

Figure 3:
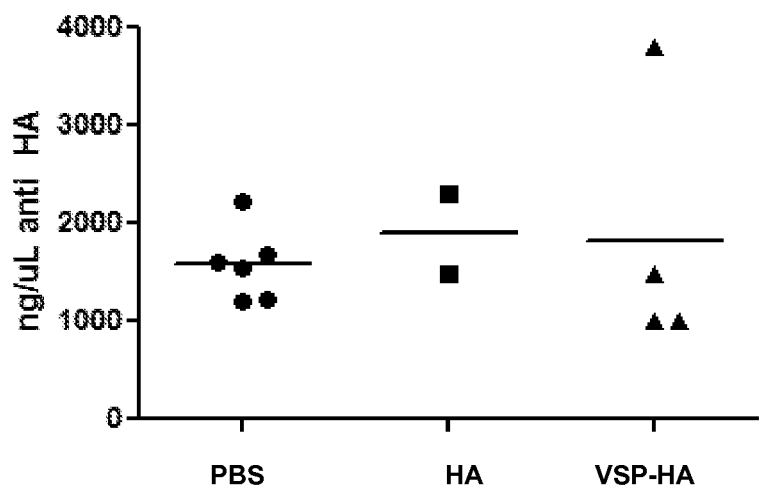

FIG. 3: Humoral immune response in mice orally vaccinated with the VSP-HA fusion protein. Enzyme-linked immunosorbent assay (ELISA). 96-well microtiter plates were coated with recombinant HA H5N1. Serial dilutions of sera were added and incubated for 2 h at RT, revealed for 1 h at RT with biotin-labeled goat Goat anti mouse Ig (H+L) (Biot. Human adsorbed. Southern Biotech Cat #1010-08), and for 1 h at RT with an ultrasensitive streptavidin-peroxidase polymer (Sigma-Aldrich). Peroxidase activity was measured using TMB substrate (Sigma-Aldrich) and optical densities were read at 450 nm (OD450) after blocking the reaction by adding HCl. The amount of anti HA were calculated based in a standard monoclonal antibody anti H5N1 HA (Mouse anti Influenza A, Avian H5N1 hemagglutinin (HA) Cat #17649-55B. USBiological).

Figure 4:
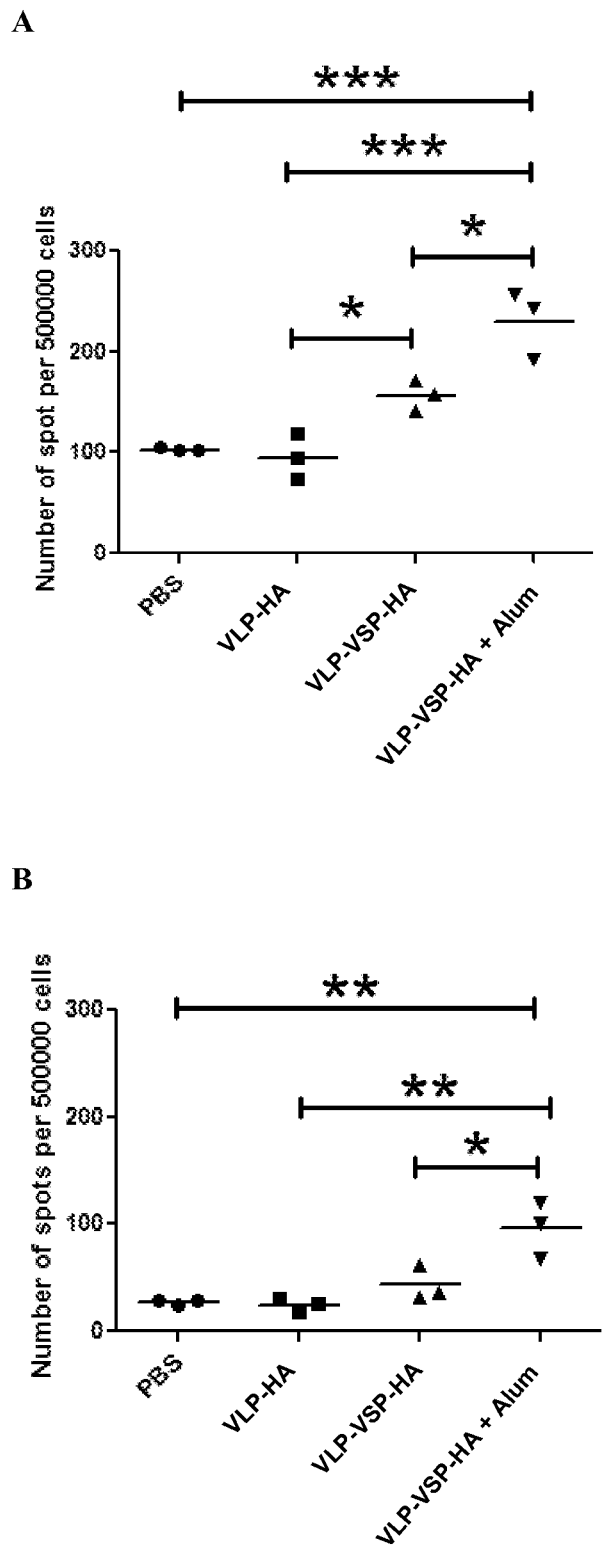

FIG. 4: ELISPOT Assay (Oral immunization with VLPs pseudotyped with HA and VSP). HA-specific IFN-γ (A) and IL-4-(B) production was determined by a standard ELISPOT assay (Mabtech, Sophia Antipolis, France). Splenocytes (5×105 cells/well) were stimulated overnight at 37° C. in 5% CO2 with 20 ng of HIV-Gag based particles pseudotyped with HA and NA†. Medium alone or concanavalin A (2 µL/mL; ConA; Sigma-Aldrich) were used as negative and positive controls, respectively. After revelation, spots were counted using the AID ELISPOT reader (ELR03, AID AutoimmunDiagnostika, Strassberg, Germany) and unspecific spots detected in the negative controls were subtracted. Symbols represent individual mice and horizontal lines represent the geometric mean of each group. *p<0.05, p<0.01, * p<0.001.

†: HIV-Gag based lentiviral particles were generated by transfection of 293T cells with expression vectors encoding the viral components (pCMV9 (Gag)+HA (pXD14)+NA (pXD15). An HIV p24-specific ELISA assay (Kit RETRO-TEK#HIV-1p24 Antigen ELISA;ZeptoMetrixCorp., New-York, USA) was used to determine the p24 concentrations in the lentiviral vector samples, according to the manufacturer's instructions.

Figure 5:
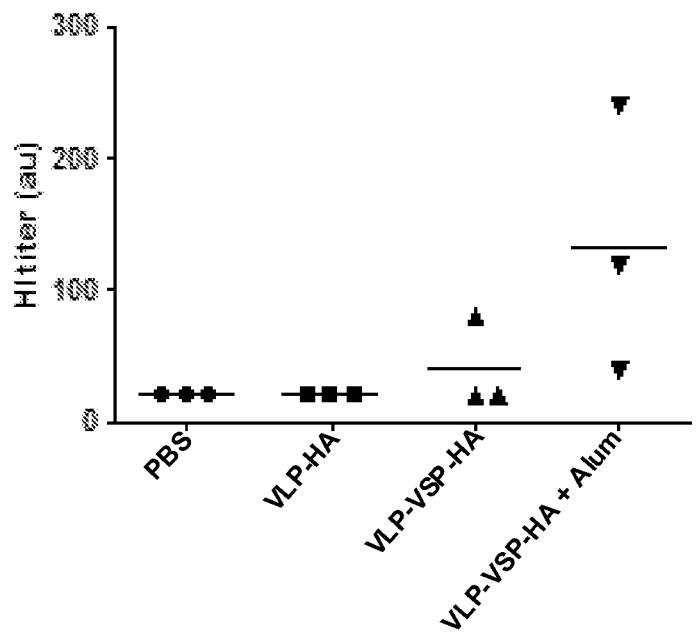

FIG. 5: Humoral immune response in mice orally vaccinated with the VLP-VSP-HA/NA. Hemagglutination inhibition (HI) antibody responses. Sera samples were serially diluted and incubated 1 h at 37° C. with 4 HA units of H5N1-pseudotyped MLV-Gag based particles in 25 µL PBS. Then, 50 µL of a 0.5% chicken erythrocyte suspension was added to each well. HI antibody titers are expressed as the reciprocal of the highest dilution of samples inhibiting agglutination. Symbols represent individual mice and horizontal lines represent the geometric mean of each group.

EXAMPLES

To obtain a proof of principle and, simultaneously, to develop a potential vaccine candidate, we used flu hemagglutinin (HA) as a model vaccinal antigen.

Therefore, to determine whether a protective and complete (T and B) immune response could be elicited by oral delivery of HA antigens carried by VSP, we constructed several vectors which would permit the concomitant expression of the VSP and the HA antigens. The HA protein from Influenza A H5N1/Hong Kong virus was used as antigen to induce B cell- and T cell-specific immune responses.

Example 1

Material & Methods

Generation of Three Different VSP/HA Constructions to be Used as Oral Vaccines:

To determine whether a protective and complete (T and B) immune response could be elicited by oral delivery of influenza hemagglutinin (HA) antigens carried by *Giardia* VSP, several constructions are made in order to permit the concomitant expression of the VSP and the HA antigens. The HA protein and its immunodominant SFE peptide are used as heterologous antigens to induce B cell- and T cell-specific immune responses, respectively.

These VSP/HA constructions include fusion proteins and virus-like particle (VLP) on which VSP and HA antigens are bound.

More precisely, three different VSP/HA constructions are thus generated, namely:

1—VSP fused to the SFE peptide to monitor T-cell specific immune responses.

2—VSP fused to the extracellular portion of HA (AHA) to monitor B-cell and T-cell specific immune responses 3—A virus-like particle (VLP) displaying VSP and HA proteins (full-length form) at its surface and/or the SFE peptide inside the particle as a gag fusion protein. VLP are formed by MLV Gag proteins fused with the SFE peptide. For displaying the VSP protein at the surface of VLPs, VSP are fused to the VSV-G transmembrane (TM) region.

Production of the VSP Fusion Proteins and Biochemical Characterization:

Control: ΔHA Alone and Polypeptide of the Invention: VSP Ex Fused to the Extracellular Portion of HA (ΔHA).

More particularly, the cDNA sequences encoding the ΔHA were derived from Influenza A H5N1 (Hong Kong). Genscript Company was hired for the production of the protein. The recombinant protein DNA sequence was codon optimized and transformed in bacteria using the company's expression vectors. Recombinant HA was obtained in the bacteria expression system using *E. coli* BL21 (DE3) strain. For purification of the HA protein a Q-column under denaturating conditions was used and the resulted protein was refolded by dialysis against 50 mM Tris-HCl, 5% Glicerol, pH 8.0.

For the production of the VSP fused to the extracellular part of the HA protein, we used HA in its soluble form—the TM region was deleted-(ΔHA). Protein sequences were analyzed using the online topology prediction platform Phobius (http://phobius.sbc.su.se/).

The full-length VSP contains a cysteine-rich extracellular region containing numerous CXXC (SEQ ID NO.: 1) motifs.

The signal peptide, the transmembrane region and the cytoplasmic 5 residues were eliminated (VSP Ex). VSP 1267 was used in these experiments.

The sequence of the fusion protein was codon optimized for the cloning into the baculovirus system. The protein was expressed and purified by one step affinity purification using the His tag present in the carboxyl terminal portion of the protein Production of the Retroviral Particles (VLP) Pseudotyped with VSP and HA at the Surface:

VLPs made from a Gag and Pseudotyped with HA and NA (Neuraminidase):

For the HA vector, the HA H5N1 (Hong Kong) sequence was cloned including its own TM domain (pXD14 vector). Wild type HA is naturally and very efficiently pseudotyped onto viral or pseudoviral particles. For NA expression the pXD15 vector was used.

VLPs Made from a Gag and Pseudotyped with VSP and HA and NA:

For pseudotyping VSP sequences onto the VLPs, the extracellular domain of the VSP was fused to the transmembrane domain (TM) of the G protein of vesicular stomatitis virus (VSV-G), which is known to be efficiently exported at the plasma membrane in mammalian cells, co-localized with Gag proteins, and be pseudotyped onto newly formed viral or pseudoviral particles (pCP1267 vector).

Note: for some experiments a Gag-Gp33-41 fusion protein was used instead of GAG, so as to measure the CD8 response. For displaying the Gp33-41 peptide inside the particle, Gp33-41 was fused to the carboxyl terminus of MLV Gag (pEB1 vector).

DNA Production:

Once all constructs were validated, plasmids were amplified and purified. The production of plasmid was done using endotoxin-free preparation kits (Nucleobond® PC 2000 EF; Macherey-Nagel, Hoerd, France).

VLP Production:

To generate recombinant retroviral particles, 293T cells were transfected with the generated expression vectors (pEB1, pCP1267, pXD15 and pXD14). Supernatants containing particles were concentrated and purified by ultracentrifugation, with or without an additional purification step by FPLC.

Each batch of VLPs was submitted to quality control analysis to validate the presence of MLV-Gag, HA or VSP by different techniques:

The functionality of the VSP-TM construct is demonstrated by its proper expression at the surface of cells transfected by the pCP1267 vector The efficiency of the VLPs production and incorporation of VSP into or onto the VLPs was assessed by Western blot on ultracentrifuged supernatant.

Results:

The correct pseudotyping of HA onto the VLPs was assessed by a hemaglutination assay. Chicken red blood cells (RBC) were incubated in presence of serial dilutions of different VLPs to evaluate agglutination in presence of a good conformational HA protein. We used VLP-HAH5N1/NA as positive control and VLP-Gag-GFP as negative control. Incubation of RBC with PBS serves to evaluate sedimentation time. By this test we showed that the VLP-VSP-HA/NA that we have developed during this study were able to promote chicken RBC agglutination.

Example 2

Material & Methods

In Vitro Validation of the Three Constructions:
2.1—At the Biochemical Level:
VSP-specific immunoprecipitation are made in order to validate the VSP-AHA and VLP constructs. Immunoprecipitates are analyzed by Western-blot. The detection of HA and the detection of HA/Gag proteins are made in order to validate the construct respectively.
2.2—At the Immunological Level:
To determine if the HA antigens can be recognized by HA-specific T cells, in vitro proliferation tests are performed with SFE-specific CD4+ T cells (obtained from the SFE transgenic mice as described in Kirberg et al. 1994), in the presence of DC sensitized with each of the three constructions or loaded with purified recombinant proteins.
Results:
We confirmed that the HA antigen present in the VLPs was correctly processed and activated HA-specific T cells by an in vitro proliferation test using CFSE labeled SFE-specific CD4+ T cells transgenic for a TCR that specifically recognizes the SFE110-119 peptide form HA (obtained from the SFE transgenic mice (Kirberg J., 1994). As observed in FIG. 1, the transgenic cells actively divide in the presence of dendritic cells (DC) pulsed with the VLP-VSP-HA, indicating that the HA protein present in the VLP has been correctly processed and presented in an MHC cII restricted way.

Example 3

Characterization of the Immune Response Anti-HA and Anti-VSP in Mice Orally Immunized by the VSP/HA Constructs The local and systemic immune responses in mice are analyzed at different time points after oral vaccination.
Model:
Mice ($H-2^d$) are immunized orally with VSP-AHA, or HA-VLPs (VSP-). As control, mice are immunized orally with ΔHA or HA-VLP (VSP-) and immunized sub-cutaneously with HA-VLPs in $Al(OH)_3$. [positive control].
Analysis:
Systemic T cell responses: Frequency of HA-specific T cells are analyzed by IFN-γ ELISPOT after HA-specific re-stimulation of the spleen cells.
Systemic B cell responses: the HA-specific antibody response are studied in serum by ELISA or inhibition hemagglutination assays.
Oral Immunization with the VSP-HA Fusion Protein:
Immunization Protocol:
Female Balb/c (H-2d) mice, 7 weeks-old received three successive oral administrations of 35 μg of the recombinant ΔHA protein or the recombinant ΔHA-VSP protein suspended in sterile PBS-Tween 20, 0.01% 3 days apart. As control, mice received vehicle only (negative control), or were once immunized s.c. with 35 ug of ΔHA in alum (positive control).
The anti-HA T cell response was analyzed in a group of mice sacrificed at day 17 (10 days after the last oral dose). The anti-HA B cell response was studied in another group of mice at day 21 (14 days after the last immunization).
Results:
Analysis of the T Cell Response:
As observed in FIG. 2, immunization with the VSP-HA fusion protein successfully induced an HA specific IFN-γ T cell response in 2 out of 2 immunized mice, as opposed to the oral immunization with the HA protein alone, which induced no significant response in 3 out of 3 vaccinated mice.

These results establish that fusion of the HA antigen to the VSP protein endows the fusion protein with the unique capacity to generate an HA antigen specific systemic T cell response when administered by the oral route.

Analysis of the B cell Response:

The generation of anti-HA specific Ab was analyzed by ELISA. Oral administration of the HA protein was unable to induce anti-HA Ab, whereas the VSP-HA fusion protein induced high titers of anti-HA Abs in one of the orally immunized mice, indicating that in the presence of the VSP, a systemic B cell response can be generated against HA (FIG. 3).

Oral Immunization with the VLPs Pseudotyped with VSP and HA at the Surface:

Immunization Protocol:

Female Balb/c (H-2d) mice, 7 weeks-old received three successive oral administrations of 35 µg of the VLP-HA/NA, VLP-VSP-HA/NA suspended in sterile PBS-Tween 20, 0.01% 3 days apart. As control, mice received vehicle only (negative control), or were once immunized s.c. with 35 ug of the VLP-VSP-HA/NA in alum (positive control).

Mice were sacrificed at day 17 (10 days after the last oral dose) and the T and B cell response to HA was analyzed.

Results:

Analysis of the T cell Response:

As observed in FIG. 4, immunization with the VLP-VSP-HA/NA fusion protein successfully induced an HA specific IFN-γ T cell response in 3 out of 3 immunized mice, as opposed to the oral immunization with the VLP-HA/NA, which induced no significant response in 3 out of 3 vaccinated mice. No significant HA-specific IL-4 production was detected, suggesting that the immune response generated by the fusion protein is of the Th1 type. These results establish that shielding the VSP-HA with the VSP protein endows the particle with the unique capacity to generate an HA antigen specific systemic T cell response when administered by the oral route.

Analysis of the B cell Response:

For the analysis of the systemic B cell responses, we quantified the HA-specific antibody response in serum using an inhibition hemagglutination assay as shown in FIG. 5. It can be seen that only VLP pseudotyped with HA and VSP can generate specific anti HA antibodies, indicating that the presence of VSP onto the VLP was necessary for the generation of a systemic anti-HA B cell response.

Conclusion

We have produced the oral vaccines composed of VSP-HA chimerical proteins or HA-expressing VLPs covered with VSPs and HA and the corresponding controls. We have biochemically validated that the VSPs and the HA proteins keep their correct conformation in the corresponding constructions. We have scaled up the production to orally immunize animals. In these experiments we have observed that contrary to the oral administration of the HA protein alone, which does not induce an specific T or B cell response, the oral administration of HA shuttled by VSPs—be as a fusion protein or in a VLP formulation-generates a HA-specific humoral and cellular response.

This work proves the validity of our strategy.

The development of this universal platform for oral delivery of vaccines should have a broad application to different infectious diseases. A great interest exists in the oral administration route, in particular for prophylactic vaccines for mass vaccination.

It results of the experiments that *Giardia* VSPs and more generally polypeptides comprising at least one CXXC motif according to the present invention seem to represent an excellent carrier to shuttle a candidate antigen trough the digestive tube to the intestine, where it may stay for a time allowing for the development of an immune response. And not least, the VSP may also act as a mucosal adjuvant, as suggested by its capacity to induce an immune response (antibodies response) by its own.

Indeed, as proof-of-principle the extracellular domain of the intestinal parasite *Giardia* VSPs as carrier to shuttle candidate antigens for oral vaccines has been shown to have the capacity to induce an effective immune response to the flu HA by oral vaccination.

REFERENCES

Throughout this application, various references describe the state of the art to which this invention pertains. The disclosures of these references are hereby incorporated by reference into the present disclosure.

Adam R D, Nigam A, Seshadri V, Martens C A, Farneth G A, Morrison H G, Nash T E, Porcella S F, Patel R; The *Giardia lamblia* vsp gene repertoire: characteristics, genomic organization, and evolution; BMC Genomics. 2010 Jul. 9; 11:424.

Franzén O, Jerlström-Hultqvist J, Castro E, Sherwood E, Ankarklev J, Reiner D S, Palm D, Andersson J O, Andersson B, Svärd S G; Draft genome sequencing of *giardia* intestinalis assemblage B isolate GS: is human giardiasis caused by two different species?; PLoS Pathog. 2009 August; 5(8):e1000560.

Hlaysa M C, Watson J C, Beach M J; Giardiasis surveillance—United States, 1998-2002; MMWR Surveill Summ. 2005 Jan. 28; 54(1):9-16.

Jerlström-Hultqvist J, Franzen O, Ankarklev J, Xu F, NohýnkováE, Andersson J O, Svärd S G, Andersson B; Genome analysis and comparative genomics of a *Giardia* intestinalis assemblage E isolate; BMC Genomics. 2010 Oct. 7; 11:543.

Kirberg J, Baron A, Jakob S, Rolink A, Karjalainen K, von Boehmer H; Thymic selection of CD8+ single positive cells with a class II major histocompatibility complex-restricted receptor; J Exp Med. 1994 Jul. 1; 180(1):25-34.

Lavelle E C, O'Hagan D T; Delivery systems and adjuvants for oral vaccines; Expert Opin. Drug Deliv. 3(6), 747-762 (2006).

Morrison H G, McArthur A G, Gillin F D, Aley S B, Adam R D, Olsen G J, Best A A, Cande W Z, Chen F, Cipriano M J, Davids B J, Dawson S C, Elmendorf H G, Hehl A B, Holder M E, Huse S M, Kim U U, Lasek-Nesselquist E, Manning G, Nigam A, Nixon J E, Palm D, Passamaneck N E, Prabhu A, Reich C I, Reiner D S, Samuelson J, Svard S G, Sogin M L; Genomic minimalism in the early diverging intestinal parasite *Giardia lamblia*; Science. 2007 Sep. 28; 317(5846):1921-6.

Nash T. E; Antigenic variation in *Giardia lamblia* and the host's immune response. Philos Trans R Soc Lond B Biol Sci 352, 1369-1375 (1997).

Nash T. E; Surface antigenic variation in *Giardia lamblia*; Mol. Microbiol. 2002 August; 45(3):585-90.

Rivero F D, Saura A, Prucca C G, Carranza P G, Torri A, Lujan H D; Disruption of antigenic variation is crucial for effective parasite vaccine; Nat Med 2010 May; 16(5):551-7.

The invention claimed is:

1. An immunogenic composition against an antigen comprising: an antigen bound to a polypeptide, wherein the polypeptide: is heterologous to the antigen, comprises 10 to 14 CXXC motifs, wherein C represents a cysteine residue and X any amino acid residue, is a variable surface protein (VSP), a VSP-like protein of a microorganism or a fragment thereof, and is able to attach to epithelial cells of the gut, and wherein CXXC corresponds to SEQ ID NO 1, wherein the microorganism is selected from the group consisting of *Giardia*, *Tetrahymena*, *Paramecium* and *Entamoeba* species, wherein the polypeptide is bound to a vector particle containing said antigen, and wherein the vector particle is a viral particle, a viral-like particle (VLP) or a nanoparticle.

2. The immunogenic composition according to claim 1 for use in oral administration.

3. The immunogenic composition according to claim 1, wherein the polypeptide is resistant to enzymatic and/or chemical degradation of the upper gastrointestinal tract.

4. The immunogenic composition according to claim 1, wherein the polypeptide is the extracellular domain of VSP or a fragment thereof.

5. The immunogenic composition according to claim 1, wherein the polypeptide is fused to said antigen.

6. The immunogenic composition according to claim 1, wherein The polypeptide is bound to a vector particle containing said antigen, and wherein the vector particle is a VLP displaying at its surface the polypeptide.

7. The immunogenic composition according to claim 6, wherein the antigen is contained inside or on the surface of the VLP.

8. The immunogenic composition according to claim 1, wherein the vector particle is a nanoparticle displaying at its surface the polypeptide and the heterologous antigen.

9. A pharmaceutical composition comprising at least the vaccine according to claim 1.

10. A method of immunization of a subject against an influenza A H5N1, wherein said method comprises administering to said subject said antigen bound to a polypeptide, wherein the polypeptide: is heterologous to said antigen, comprises 10 to 14 CXXC motifs, wherein C represents a cysteine residue and X any amino acid residue, is a variable surface protein (VSP), a VSP-like protein of a microorganism or a fragment thereof, and is able to attach to epithelial cells of the gut, and wherein CXXC corresponds to SEQ ID NO 1, wherein the microorganism is selected from the group consisting of *Giardia*, *Tetrahymena*, *Paramecium* and *Entamoeba* species, wherein the polypeptide is bound to a vector particle containing said antigen, and wherein the vector particle is a viral particle, a viral-like particle (VLP) or a nanoparticle.

11. The method of claim 10, wherein said antigen bound to a polypeptide is administered by oral route.

\* \* \* \* \*